United States Patent
Surendran et al.

(10) Patent No.: US 10,706,302 B2
(45) Date of Patent: Jul. 7, 2020

(54) REAL TIME VEHICLE OCCUPANT EMERGENCY HEALTH DATA SYSTEMS AND METHODS

(71) Applicant: Volvo Car Corporation, Göteborg (SE)

(72) Inventors: Aswathy Surendran, Mountain View, CA (US); Peter Winzell, Mountain View, CA (US)

(73) Assignee: Volvo Car Corporation, Göteborg (SE)

( * ) Notice: Subject to any disclaimer, the term of this patent is extended or adjusted under 35 U.S.C. 154(b) by 0 days.

(21) Appl. No.: 15/995,657

(22) Filed: Jun. 1, 2018

(65) Prior Publication Data

US 2019/0370576 A1    Dec. 5, 2019

(51) Int. Cl.
| | |
|---|---|
| *G06K 9/00* | (2006.01) |
| *G16H 10/60* | (2018.01) |
| *G16H 50/20* | (2018.01) |
| *G16H 80/00* | (2018.01) |

(52) U.S. Cl.
CPC ..... *G06K 9/00845* (2013.01); *G06K 9/00288* (2013.01); *G16H 10/60* (2018.01); *G16H 50/20* (2018.01); *G16H 80/00* (2018.01)

(58) Field of Classification Search
CPC .................................................. G06K 9/00845
USPC ...................................................... 340/573.1
See application file for complete search history.

(56) References Cited

U.S. PATENT DOCUMENTS

| | | | | |
|---|---|---|---|---|
| 7,676,062 B2* | 3/2010 | Breed | ............... | B60R 21/01552 382/100 |
| 8,335,616 B2* | 12/2012 | Neal | ....................... | B60R 25/00 180/271 |
| 9,317,983 B2* | 4/2016 | Ricci | .................. | G06Q 30/0266 |

(Continued)

FOREIGN PATENT DOCUMENTS

| | | |
|---|---|---|
| EP | 2743141 A1 | 6/2014 |
| EP | 2860652 A2 | 4/2015 |

OTHER PUBLICATIONS

Sep. 30, 2019 Extended European Search Report issued on European Application 19177573.

*Primary Examiner* — Qutbuddin Ghulamali
(74) *Attorney, Agent, or Firm* — Clements Bernard Walker; Christopher L. Bernard

(57) ABSTRACT

Real time vehicle occupant emergency health data systems and methods that link a vehicle subsystem, a cloud subsystem, and a public health profile subsystem such that, in a triggering vehicle emergency event or the like, the health status of a previously-identified or unidentified vehicle occupant is captured in real time by an on-board camera and/or other sensor. This vehicle occupant identification and health status information are variously transmitted to the cloud, where the vehicle occupant identification is coupled with available public health profile information, in the case of a previously-identified vehicle occupant. Subsequently, the health status information and public health profile information are transmitted to an emergency responder or the like, thereby aiding in rendering medical assistance to an injured (Continued)

or sick vehicle occupant. The systems and methods of the present disclosure may also provide data analytics information that may be used later to improve vehicle safety.

18 Claims, 3 Drawing Sheets

(56) References Cited

U.S. PATENT DOCUMENTS

| | | | |
|---|---|---|---|
| 2013/0158778 A1* | 6/2013 | Tengler | G08G 1/096716 701/31.5 |
| 2016/0152180 A1* | 6/2016 | Kirsch | B60Q 9/00 701/36 |
| 2017/0365106 A1* | 12/2017 | Lei | A61B 5/746 |

* cited by examiner

REAL TIME VEHICLE OCCUPANT EMERGENCY HEALTH DATA SYSTEMS AND METHODS

FIELD OF THE DISCLOSURE

The present disclosure relates generally to the vehicle safety field. More specifically, the present disclosure relates to real time vehicle occupant emergency health data systems and methods. The present disclosure links a vehicle subsystem, a cloud subsystem, and a public health profile subsystem such that, in a triggering vehicle emergency event or the like, the health status of a previously-identified or unidentified vehicle occupant is captured in real time by an on-board camera and/or other sensor. This vehicle occupant identification and health status information are variously transmitted to the cloud, where the vehicle occupant identification is coupled with available public health profile information, in the case of a previously-identified vehicle occupant. Subsequently, the health status information and public health profile information are transmitted to an emergency responder or the like, thereby aiding in rendering medical assistance to an injured or sick vehicle occupant. The systems and methods of the present disclosure may also provide data analytics information that may be used later to improve vehicle safety.

BACKGROUND OF THE DISCLOSURE

The connected vehicle infrastructure provides a platform for collecting and utilizing much vehicle data that can be used advantageously in a wide variety of applications. Such applications are not limited to vehicle control and infotainment, but may also involve vehicle safety. One such safety issue is the availability of situational awareness and adequate medical information in an accident or other emergency situation.

Different vehicle manufacturers have different telematic solutions for identifying accidents and other emergency situations and triggering the automatic dispatch of emergency personnel. Most of these solutions involve sensing the deployment of airbags or monitoring other on-board sensors and opening a communication channel with a potentially injured or sick vehicle occupant. Thus, limited event and medical information may be relayed to the emergency personnel. No known solutions identify a vehicle occupant in advance of an emergency event or the like and provide his or her relevant medical history to the emergency personnel upon the occurrence of a triggering event. Importantly, such information would allow the emergency personnel to more quickly and effectively treat an injured or sick vehicle occupant on scene, and later at a medical facility. It is not always possible to obtain this information from the vehicle occupant when a triggering event occurs, as he or she may be unconscious or traumatized, depending on the severity of the triggering event. Critical information may include, for example: identity, sex, age, personal statistics, blood type, medications, allergies, pre-existing conditions, pregnancy status, physicians, emergency contact information, and the like, in addition to vehicle type and location, vehicle occupant seating position, and vehicle occupant condition.

Thus, what are still needed in the art are systems and methods that, in a triggering vehicle emergency event or the like, capture the health status of a previously-identified or unidentified vehicle occupant in real time using an on-board camera and/or other sensor. Preferably, this vehicle occupant identification and health status information are variously transmitted to the cloud, where the vehicle occupant identification is coupled with available public health profile information, in the case of a previously-identified vehicle occupant. Subsequently, the health status information and public health profile information are transmitted to an emergency responder or the like, thereby aiding in rendering medical assistance to an injured or sick vehicle occupant.

BRIEF SUMMARY OF THE DISCLOSURE

Accordingly, in various exemplary embodiments, the present disclosure provides systems and methods that, in a triggering vehicle emergency event or the like, capture the health status of a previously-identified or unidentified vehicle occupant in real time using an on-board camera and/or other sensor. This vehicle occupant identification and health status information are transmitted to the cloud, where the vehicle occupant identification is coupled with available public health profile information, in the case of a previously-identified vehicle occupant. Subsequently, the health status information and public health profile information are transmitted to an emergency responder or the like, thereby aiding in rendering medical assistance to an injured or sick vehicle occupant. The systems and methods of the present disclosure may also provide data analytics information that may be used later to improve vehicle safety.

When a vehicle occupant enters a vehicle, he or she is first detected and then identified by the vehicle subsystem, using an interior camera and a facial recognition algorithm or the like, a near-field mobile device identification methodology, a self-identification user interface, or the like. This identification process may be supplemented by one or more pre-populated likely vehicle occupant databases resident in the cloud subsystem. In any event, the vehicle subsystem provides a real time vehicle occupant list or map (optionally also generated using one or more on-board vehicle occupant position sensors or the like) that is transmitted to and maintained by the cloud subsystem. This real time vehicle occupant list or map is associated with a given vehicle identifier, for example. Thus, at all times, the cloud subsystem monitors who is in a particular vehicle and, preferably, where they are seated in the vehicle.

In the cloud subsystem, which contains one or more databases of public health profile information and/or is in communication with a remote public health profile subsystem, each previously-identified vehicle occupant is associated with his or her public health profile, and this information is made available for later use with (prior or contemporaneous) vehicle occupant consent. Again, critical information may include, for example: identity, sex, age, personal statistics, blood type, medications, allergies, pre-existing conditions, pregnancy status, physicians, emergency contact information, and the like, in addition to vehicle type and location, vehicle occupant seating position, and vehicle occupant condition.

In a triggering vehicle emergency event or the like, the health status of a previously-identified or unidentified vehicle occupant is captured in real time by the interior camera and/or other sensor and this health status information is transmitted to the cloud subsystem. Subsequently, the health status information and public health profile information associated with a previously-identified vehicle occupant are transmitted to the emergency responder or the like, thereby aiding in rendering medical assistance to an injured or sick vehicle occupant. This communication may occur automatically over a pre-established communication link or it may be requested by the emergency responder, and may also include relevant vehicle identification and location information. Thus, when an emergency responder arrives on scene, he or she already knows what vehicle to look for, who (specifically or generally) is inside and where they are seated, their current medical condition, and their relevant medical history. This is all critical information and may be supplemented as necessary.

Current health status may be assessed at the vehicle subsystem level or the cloud subsystem level manually by a system operator or automatically using one or more camera and/or sensor-based artificial intelligence algorithms operable for detecting movement and/or assessing the general state of health of a person. Again, the systems and methods of the present disclosure may also provide data analytics information that may be used later to improve vehicle safety. For example, the systems and methods of the present disclosure, coupled with other telematics systems and methods, provide very specific information related to what types of injuries occur in what types of accidents. Such knowledge is useful for design purposes.

In one exemplary embodiment, the present disclosure provides a vehicle occupant emergency health data system, including: a vehicle occupant identification subsystem operable for detecting and identifying a vehicle occupant present in a vehicle with a predetermined vehicle identification for a ride, wherein the vehicle occupant identification subsystem is further operable for determining a seating position of the detected and identified vehicle occupant; a public health profile data association subsystem operable for associating predetermined public health profile data with the detected and identified vehicle occupant; one or more of a camera and a sensor operable for obtaining health status information from the detected and identified vehicle occupant responsive to the occurrence of an emergency event; and, optionally, a communication link operable for transmitting one or more of the predetermined public health profile data and the health status information of the detected and identified vehicle occupant to an emergency responder or other third party corresponding to the occurrence of the emergency event. The vehicle occupant identification subsystem includes a processor executing one or more of a facial recognition algorithm, a near-field mobile device identification algorithm, and a self-identification algorithm. The vehicle occupant identification subsystem is further operable for tagging the presence and relative seating position of an unidentified vehicle occupant to the predetermined vehicle identification. The one or more of the camera and the sensor are further operable for obtaining health status information from the unidentified vehicle occupant responsive to the occurrence of the emergency event and the communication link is further operable for transmitting the health status information of the unidentified vehicle occupant to the emergency responder or other third party corresponding to the occurrence of the emergency event. Optionally, the health status information includes a camera image. A vehicle occupant injury state is determined by one or more of a system operator observing the camera image and an artificial intelligence algorithm analyzing the camera image. The vehicle occupant identification subsystem includes one or more of a vehicle subsystem and a cloud subsystem. The communication link couples one or more of the cloud subsystem and the public health profile data association subsystem directly or indirectly to the emergency responder or other third party. The health status information includes one or more of identity, sex, age, personal health information and statistics, blood type, medications, allergies, pre-existing conditions, pregnancy status, physicians, and emergency contact information. The one or more of the predetermined public health profile data and the health status information are provided to the emergency responder or other third party with prior consent of the vehicle occupant.

In another exemplary embodiment, the present disclosure provides a vehicle occupant emergency health data method, including: detecting and identifying a vehicle occupant present in a vehicle with a predetermined vehicle identification for a ride using a vehicle occupant identification subsystem, and determining a seating position of the detected and identified vehicle occupant using the vehicle occupant identification subsystem; associating predetermined public health profile data with the detected and identified vehicle occupant using a public health profile data association subsystem; obtaining health status information from the detected and identified vehicle occupant responsive to the occurrence of an emergency event using one or more of a camera and a sensor; and transmitting one or more of the predetermined public health profile data and the health status information of the detected and identified vehicle occupant to an emergency responder or other third party corresponding to the occurrence of the emergency event using a communication link. The vehicle occupant identification subsystem includes a processor executing one or more of a facial recognition algorithm, a near-field mobile device identification algorithm, and a self-identification algorithm. The method further includes tagging the presence and relative seating position of an unidentified vehicle occupant to the predetermined vehicle identification using the vehicle occupant identification subsystem. The method further includes obtaining health status information from the unidentified vehicle occupant responsive to the occurrence of the emergency event using the one or more of the camera and the sensor and transmitting the health status information of the unidentified vehicle occupant to the emergency responder or other third party corresponding to the occurrence of the emergency event using the communication link. Optionally, the health status information includes a camera image. A vehicle occupant injury state is determined by one or more of a system operator observing the camera image and an artificial intelligence algorithm analyzing the camera image. The vehicle occupant identification subsystem includes one or more of a vehicle subsystem and a cloud subsystem. The communication link couples one or more of the cloud subsystem and the public health profile data association subsystem directly or indirectly to the emergency responder or other third party. The health status information includes one or more of identity, sex, age, personal health information and statistics, blood type, medications, allergies, pre-existing conditions, pregnancy status, physicians, and emergency contact information. The one or more of the predetermined public health profile data and the health status information are provided to the emergency responder or other third party with prior consent of the vehicle occupant.

BRIEF DESCRIPTION OF THE DRAWINGS

The present disclosure is illustrated and described herein with reference to the various drawings, in which like reference numbers are used to denote like system components/method steps, as appropriate, and in which.

DETAILED DESCRIPTION OF THE DISCLOSURE

Figure 1:
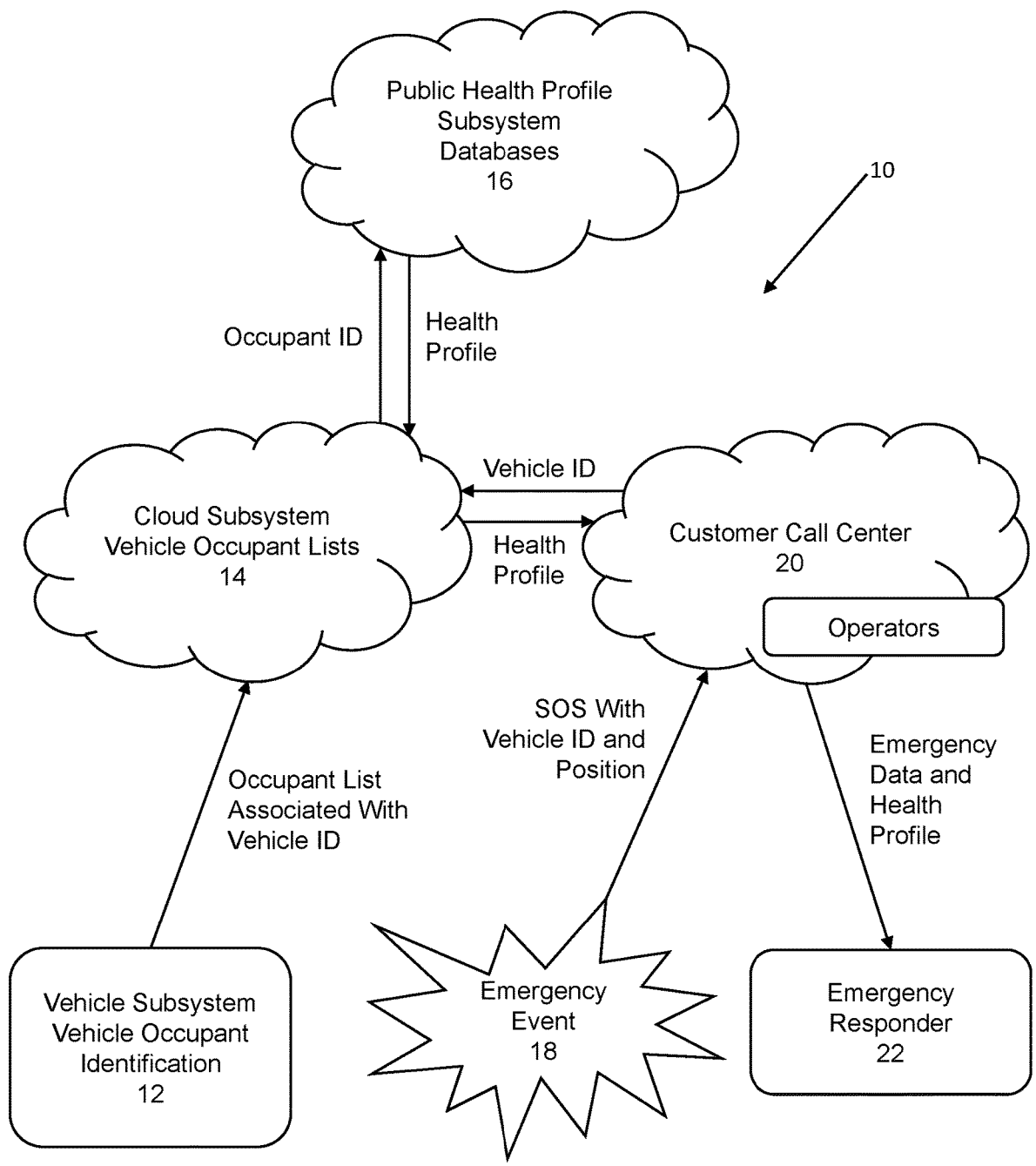
FIG. 1 is a schematic diagram illustrating one exemplary embodiment of the real time vehicle occupant emergency health data system/method of the present disclosure.

Referring now specifically to FIG. 1, in one exemplary embodiment of the present disclosure, the real time vehicle occupant emergency health data system 10 provides a means to tag a vehicle ID with vehicle occupant details and health data during a vehicle ride, utilizing a method for identifying each vehicle occupant without necessarily requiring affirmative action on his or her part. This is important as vehicle occupants can normally be expected to forget or decline to affirmatively identify themselves for a vehicle ride.

Vehicle occupant identification in the vehicle subsystem 12 is triggered by the detection of a vehicle occupant in a given vehicle. Specifically, vehicle occupant identification may be triggered by a seat sensor, a seatbelt sensor, a camera image, or the like indicating that a vehicle occupant has entered the vehicle. Subsequent to a vehicle occupant being detected, one or more interior cameras mounted at a predetermined locations within the vehicle obtain images of each vehicle occupant. These images are then analyzed using a facial recognition algorithm or the like, such that the identity of each vehicle occupant in each location in the vehicle is determined. Alternatively, or in addition, near-field mobile device communication or the like may be used to ascertain the identity of each vehicle occupant based on mobile device tagging. Further, a manual check-in or self-identification process may be used to supplement these methodologies.

Vehicle occupant identification may ultimately take place locally in the vehicle subsystem 12, or it may take place remotely in the cloud subsystem 14. In either case, the camera image or other identifying information is ultimately checked against one or more databases of known potential vehicle occupants to identify each vehicle occupant. These vehicle occupant identities are tagged to the relevant vehicle ID and the relative position of each vehicle occupant within the vehicle. If these determinations are made within the vehicle subsystem 12, then this data is synced to the cloud subsystem 14 as appropriate. For example, vehicle occupant identification may be triggered by the activation of a seat or seatbelt sensor, and then data transfer to the cloud subsystem 14 may be triggered by the activation of the vehicle ignition. Other triggering events may be used equally.

An unknown vehicle occupant is also tagged, along with a relevant seating position, to the relevant vehicle ID and monitored by the camera(s) and other sensors, when used.

Upon the occurrence of an emergency event, such as a crash with the deployment of airbags or the like, conventional emergency cloud notification occurs, communication with a system operator may be opened, and the camera(s) and/or other sensors monitor each vehicle occupant for their real time health status. Specifically, from camera images, for example, it may be possible to determine whether a vehicle occupant is conscious and to what extent he or she has been injured in a broad sense. This health status information is uploaded to the cloud subsystem 14 for further processing and use, as described in greater detail herein below.

A vehicle occupant ride list is maintained for each ride in the cloud subsystem 14, providing a real time list of vehicle IDs, identified vehicle occupants, unidentified vehicle occupants (if any), and the relative seating position of each vehicle occupant. This provides a vehicle to vehicle occupant mapping during the lifecycle of each ride. This list is maintained and updated based on status notifications and event-driven updates from the vehicle subsystem 12 as vehicle occupants change, health statuses change, etc. Related to health status, the cloud subsystem 14 may also implement an artificial intelligence algorithm for ascertaining each vehicle occupant's health status from the relevant camera images and/or other data. Alternatively, this process may be carried out at the vehicle subsystem level. Further, it may be carried out manually by a system operator, emergency responder, or the like based on obtained images or other data.

Preferably, the cloud subsystem 14 is in communication with a public health profile subsystem 16 such that public health profile data can be collected when needed and made available as appropriate. There is no visible mapping between a vehicle occupant and his or her private health profile data. A subset of the vehicle occupant's private health profile data forms a public health profile and is made available as the public health profile data used, with prior consent. The public health profile data is accessed by paramedics in the case of an emergency anywhere, not just inside the vehicle. This public health profile data may be hosted by an original equipment manufacturer (OEM), a hospital, an insurance company, a third party service provider, a social networking platform, or the like. This data subset has the capability to provide a secure application program interface (API) to authenticate a request including a vehicle occupant ID to the associated server and respond with the emergency data.

If public health data is not otherwise available, an OEM or other party can create their own private cloud that hosts the relevant public health profile data. Accordingly, all users are asked to provide a one-time informational profile, and perhaps periodically update it, to build and maintain their profile. A user can do this when he or she registers as a vehicle owner, for example, or when a vehicle is rented, etc. Repositories can be created such that public health profile data is available for an individual as they move from enabled vehicle to enabled vehicle.

As illustrated, upon the occurrence of an emergency event 20, such as the deployment of airbags in a vehicle accident or the like, a conventional SOS message or emergency alert, including the vehicle ID and location, is relayed from the vehicle to the customer call center 20 or other central office. At this time, the camera/sensor health status of each previously-identified and unidentified vehicle occupant may also be captured and relayed to the cloud subsystem 14 and customer call center 20, along with the now appended public health profile data, if available. Subsequently, either manually, automatically, or by request, the public health profile data and/or health status of each previously-identified and unidentified vehicle occupant are relayed to the emergency responder 22, along with the conventional vehicle and location information. Vehicle occupant identification is also potentially relayed as part of the public health profile data. Information may be relayed to the emergency responder through his or her dispatch center, emergency vehicle, and/or a mobile device running an appropriate application.

Figure 2:
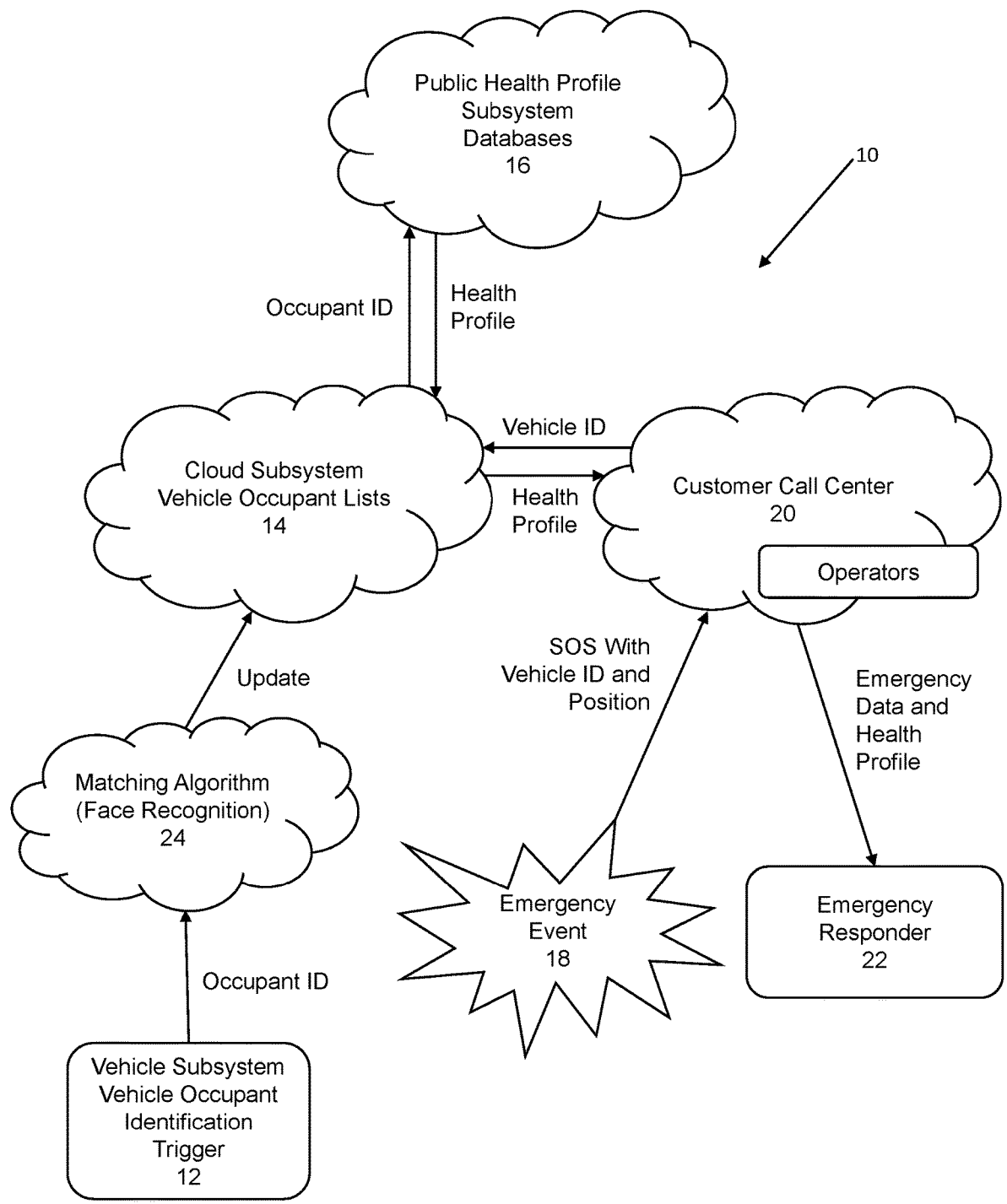
FIG. 2 is a schematic diagram illustrating another exemplary embodiment of the real time vehicle occupant emergency health data system/method of the present disclosure.

FIG. 2 illustrates an alternative embodiment in which the vehicle occupant matching algorithm 24 is remote from the vehicle subsystem 12 and the cloud subsystem 14 described herein. The vehicle subsystem 12 transmits a unique vehicle occupant ID to the vehicle occupant matching algorithm 24 for each sensed/imaged vehicle occupant. Vehicle occupant updates are then transmitted to the cloud subsystem 14 for maintaining the vehicle occupant ride lists, associating the appropriate public health profiles, and providing them to emergency responders 22 accordingly.

Figure 3:
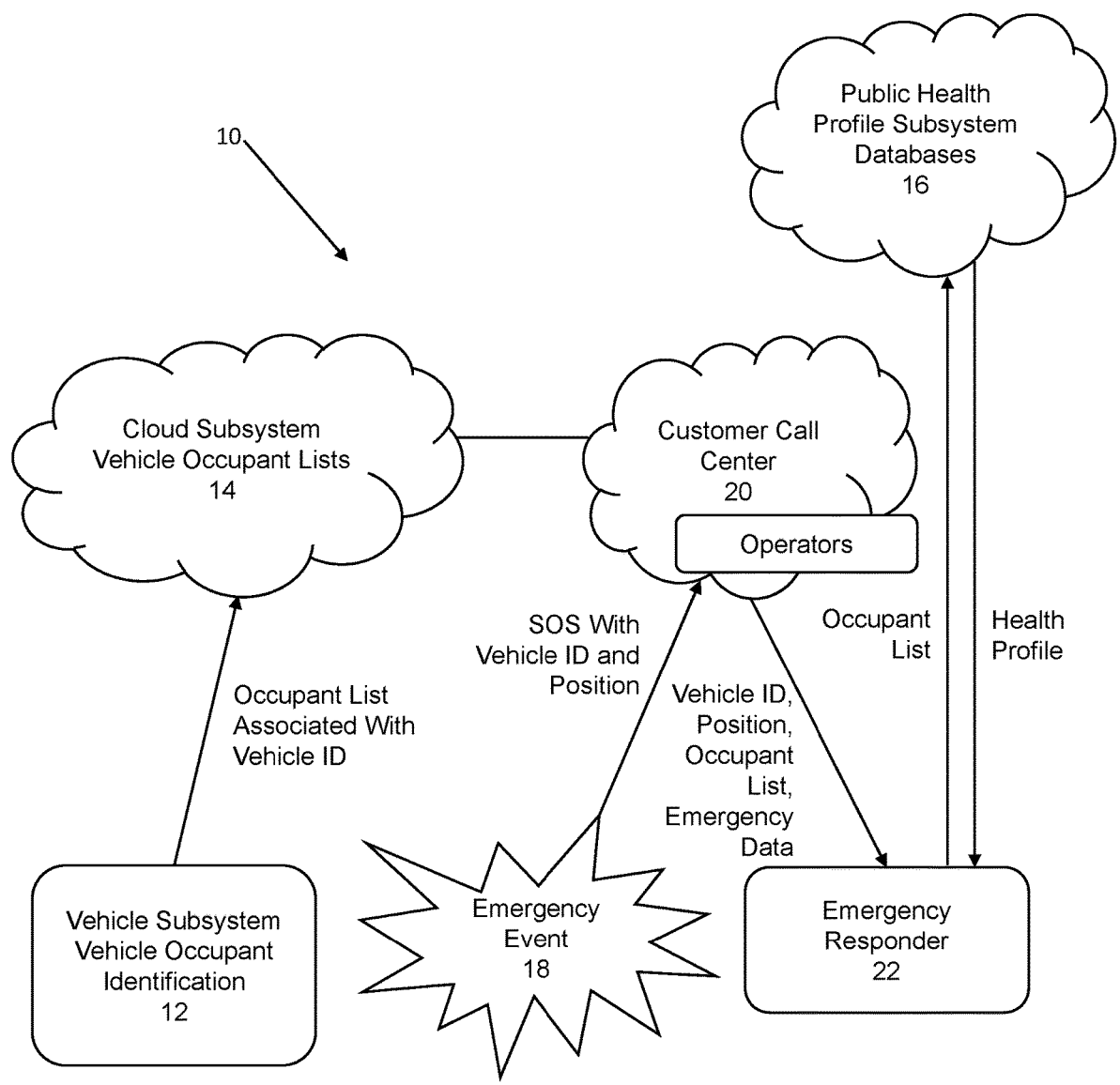
FIG. 3 is a schematic diagram illustrating a further exemplary embodiment of the real time vehicle occupant emergency health data system/method of the present disclosure.

FIG. 3 illustrates an alternative embodiment in which, after receiving a vehicle ID, location, and vehicle occupant list, health statuses, and potentially other emergency data from a call center 20 and/or the cloud subsystem 14, the emergency responder 22 obtains public health profile data directly from the public health profile subsystem 16. This public health profile data is not necessarily shared with the call center 20 and/or the cloud subsystem 14. Here, the vehicle subsystem 12 and cloud subsystem 14 are collectively primarily operable for generating and updating the vehicle occupant list and providing the associated health statuses when and to whom appropriate.

Preferably, the software applications of the present disclosure are each implemented as coded instructions stored in a memory and executed by a processor. The processor is a hardware device, such as a server, for executing such coded instructions. The processor can be any custom made or commercially available processor, a central processing unit (CPU), an auxiliary processor among several processors associated with the memory, a semiconductor-based microprocessor (in the form of a microchip or chip set), or generally any device for executing coded instructions. The processor is configured to execute software stored within the memory, to communicate data to and from the memory, and to generally control operations pursuant to the coded instructions. In an exemplary embodiment, the processor may include a mobile optimized processor, such as one optimized for power consumption and mobile applications. I/O interfaces can be used to receive user input and/or for providing system output. User input can be provided via, for example, a keypad, a touch screen, a scroll ball, a scroll bar, buttons, and/or the like. System output can be provided via a display device, such as a liquid crystal display (LCD), touch screen, and/or the like. The I/O interfaces can also include, for example, a serial port, a parallel port, a small computer system interface (SCSI), an infrared (IR) interface, a radio frequency (RF) interface, a universal serial bus (USB) interface, and/or the like. The I/O interfaces can include a graphical user interface (GUI) that enables a user to interact with the memory. Additionally, the I/O interfaces may further include an imaging device, i.e. the camera, a video camera, various sensors, etc.

The memory may include any of volatile memory elements (e.g., random access memory (RAM, such as DRAM, SRAM, SDRAM, etc.)), nonvolatile memory elements (e.g., ROM, hard drive, etc.), and combinations thereof. Moreover, the memory may incorporate electronic, magnetic, optical, and/or other types of storage media. Note that the memory may have a distributed architecture, where various components are situated remotely from one another, but can be accessed by the processor. The software in memory can include one or more software programs, each of which includes an ordered listing of executable instructions for implementing logical functions. The software in the memory includes a suitable operating system (O/S) and programs. The operating system essentially controls the execution of other computer programs, and provides scheduling, input-output control, file and data management, memory management, and communication control and related services. The programs may include various applications, add-ons, etc. configured to provide end user functionality. The programs can include an application or "app" which provides various functionality.

Accordingly, in various exemplary embodiments, the present disclosure provides systems and methods that, in a triggering vehicle emergency event or the like, capture the health status of a previously-identified or unidentified vehicle occupant in real time using an on-board camera and/or other sensor. This vehicle occupant identification and health status information are transmitted to the cloud, where the vehicle occupant identification is coupled with available public health profile information, in the case of a previously-identified vehicle occupant. Subsequently, the health status information and public health profile information are transmitted to an emergency responder or the like, thereby aiding in rendering medical assistance to an injured or sick vehicle occupant. The systems and methods of the present disclosure may also provide data analytics information that may be used later to improve vehicle safety.

When a vehicle occupant enters a vehicle, he or she is identified by the vehicle subsystem, using an interior camera and a facial recognition algorithm or the like, a near-field mobile device identification methodology, a self-identification user interface, or the like. This identification process may be supplemented by one or more pre-populated potential vehicle occupant databases resident in the cloud subsystem. In any event, the vehicle subsystem provides a real time vehicle occupant list or map (optionally also generated using one or more on-board vehicle occupant position sensors or the like) that is transmitted to and maintained by the cloud subsystem. This real time vehicle occupant list or map is associated with a given vehicle identifier, for example. Thus, at all times, the cloud subsystem monitors who is in a particular vehicle and, preferably, where they are seated in the vehicle.

In the cloud subsystem, which contains one or more databases of public health profile information and/or is in communication with a remote public health profile subsystem, each previously-identified vehicle occupant is associated with his or her public health profile, and this information is made available for later use with (prior or contemporaneous) vehicle occupant consent. Again, critical information may include, for example: identity, sex, age, personal statistics, blood type, medications, allergies, pre-existing conditions, pregnancy status, physicians, emergency contact information, and the like.

In a triggering vehicle emergency event or the like, the health status of a previously-identified or unidentified vehicle occupant is captured in real time by the interior camera and/or other sensor and this health status information is transmitted to the cloud subsystem. Subsequently, the health status information and public health profile information associated with a previously-identified vehicle occupant are transmitted to the emergency responder or the like, thereby aiding in rendering medical assistance to an injured or sick vehicle occupant. This communication may occur automatically over a pre-established communication link or it may be requested by the emergency responder, and may also include relevant vehicle identification and location information. Thus, when an emergency responder arrives on scene, he or she already knows what vehicle to look for, who (specifically or generally) is inside and where they are seated, their current medical condition, and their relevant medical history. This is all critical information for emergency responders and healthcare providers.

Current health status may be assessed at the vehicle subsystem level or the cloud subsystem level manually by a system operator or automatically using one or more camera and/or sensor-based artificial intelligence algorithms operable for detecting movement and/or assessing the general state of health of a person. Again, the systems and methods of the present disclosure may also provide data analytics information that may be used later to improve vehicle safety. For example, the systems and methods of the present disclosure, coupled with other telematics systems and methods, provide very specific information related to what types of injuries occur in what types of accidents. Such knowledge is useful for design purposes.

Although the present disclosure is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following non-limiting claims for all purposes.

What is claimed is:

1. A vehicle occupant emergency health data system, comprising:
   a vehicle occupant identification subsystem operable for identifying a vehicle occupant present in a vehicle with a predetermined vehicle identification for a ride;
   a public health profile data association subsystem operable for associating predetermined public health profile data with the identified vehicle occupant;
   a camera operable for obtaining an image of the identified vehicle occupant and monitoring real time health status information from the identified vehicle occupant responsive to the occurrence of an emergency event, wherein the health status information comprises a real time vehicle occupant injury state determined by an artificial intelligence algorithm executed in a vehicle subsystem or a cloud subsystem analyzing the camera image to assess present movement and an injury state of the identified vehicle occupant; and
   a communication link operable for transmitting the predetermined public health profile data, the camera image, and the health status information of the identified vehicle occupant to an emergency responder or other third party corresponding to the occurrence of the emergency event.

2. The system of claim 1, wherein the vehicle occupant identification subsystem is further operable for determining a seating position of the identified vehicle occupant.

3. The system of claim 1, wherein the vehicle occupant identification subsystem comprises a processor executing one or more of a facial recognition algorithm, a near-field mobile device identification algorithm, and a self-identification algorithm.

4. The system of claim 1, wherein the vehicle occupant identification subsystem is further operable for tagging the presence and relative seating position of an unidentified vehicle occupant to the predetermined vehicle identification.

5. The system of claim 4, wherein the camera is further operable for obtaining an image and health status information from the unidentified vehicle occupant responsive to the occurrence of the emergency event and the communication link is further operable for transmitting the camera image and the health status information of the unidentified vehicle occupant to an emergency responder or other third party corresponding to the occurrence of the emergency event.

6. The system of claim 1, wherein the vehicle occupant identification subsystem comprises one or more of a vehicle subsystem and a cloud subsystem.

7. The system of claim 6, wherein a communication link couples one or more of the cloud subsystem and the public health profile data association subsystem directly or indirectly to an emergency responder or other third party.

8. The system of claim 1, wherein the predetermined public health profile data comprises one or more of identity, sex, age, personal health information and statistics, blood type, medications, allergies, pre-existing conditions, pregnancy status, physicians, and emergency contact information.

9. The system of claim 1, wherein the predetermined public health profile data and the health status information are provided to the emergency responder or other third party with prior obtained consent of the vehicle occupant.

10. A vehicle occupant emergency health data method, comprising:
    identifying a vehicle occupant present in a vehicle with a predetermined vehicle identification for a ride using a vehicle occupant identification subsystem;
    associating predetermined public health profile data with the identified vehicle occupant using a public health profile data association subsystem;
    obtaining, by a camera, an image of the identified vehicle occupant and monitoring real time health status information from the identified vehicle occupant responsive to the occurrence of an emergency event, wherein the health status information comprises a real time vehicle occupant injury state determined by an artificial intelligence algorithm executed in a vehicle subsystem or a cloud subsystem analyzing the camera image to assess present movement and an injury state of the identified vehicle occupant; and
    transmitting the predetermined public health profile data, the camera image, and the health status information of the identified vehicle occupant to an emergency responder or other third party corresponding to the occurrence of the emergency event.

11. The method of claim 10, further comprising determining a seating position of the identified vehicle occupant using the vehicle occupant identification subsystem.

12. The method of claim 10, wherein the vehicle occupant identification subsystem comprises a processor executing one or more of a facial recognition algorithm, a near-field mobile device identification algorithm, and a self-identification algorithm.

13. The method of claim 10, further comprising tagging the presence and relative seating position of an unidentified vehicle occupant to the predetermined vehicle identification using the vehicle occupant identification subsystem.

14. The method of claim 13, further comprising obtaining an image and health status information from the unidentified vehicle occupant responsive to the occurrence of the emergency event and the communication link is further operable for transmitting the camera image and the health status information of the unidentified vehicle occupant to an emergency responder or other third party corresponding to the occurrence of the emergency event.

15. The method of claim 10, wherein the vehicle occupant identification subsystem comprises one or more of a vehicle subsystem and a cloud subsystem.

16. The method of claim 15, wherein the communication link couples one or more of the cloud subsystem and the public health profile data association subsystem directly or indirectly to the emergency responder or other third party.

17. The method of claim 10, wherein the predetermined public health profile data comprises one or more of identity, sex, age, personal health information and statistics, blood type, medications, allergies, pre-existing conditions, pregnancy status, physicians, and emergency contact information.

18. The method of claim 10, wherein the predetermined public health profile data and the health status information are provided to the emergency responder or other third party with prior obtained consent of the vehicle occupant.

* * * * *